(12) United States Patent
Kashiwagi (10) Patent No.: US 6,471,682 B2
(45) Date of Patent: Oct. 29, 2002

(54) ABSORBENT ARTICLE

(75) Inventor: Masahiro Kashiwagi, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 12 days.

(21) Appl. No.: 09/791,022

(22) Filed: Feb. 22, 2001

(65) Prior Publication Data

US 2001/0021836 A1 Sep. 13, 2001

(30) Foreign Application Priority Data

Mar. 7, 2000 (JP) ........................................ 2000-062133

(51) Int. Cl.[7] ................................................. A61F 13/15
(52) U.S. Cl. .......................... 604/385.27; 604/385.16; 604/385.01; 604/378; 604/385.31
(58) Field of Search ...................... 604/385.27, 385.16, 604/385.01, 378, 385.31

(56) References Cited

U.S. PATENT DOCUMENTS 5,593,400 A * 1/1997 O'Leary ................. 604/385.02
5,853,403 A * 12/1998 Tanzer ................... 604/385.01

FOREIGN PATENT DOCUMENTS

| EP | 0357298 A2 | 3/1996 |
| JP | 1.7-33315 | 6/1995 |
| WO | WO-98/29074 | 7/1998 |

* cited by examiner

*Primary Examiner*—Rodney M. Lindsey
*Assistant Examiner*—Angela J Grayson
(74) *Attorney, Agent, or Firm*—Darby & Darby (57) ABSTRACT

There is disclosed an absorbent article including: a liquid absorbing member having an absorbent core; a support body positioned on the lower side of the liquid absorbing member; and an elastic member for supporting the liquid absorbing member. The elastic member extends in the longitudinal direction of the absorbent article and is fixed at its front and rear end portions on the support body. The elastic member is positioned at the widthwise central portion of the absorbent article. The support body is bent in the longitudinal direction by the tension of the elastic member, and the liquid absorbing member is deformed to bulge at its widthwise central portion away from the support body by the central elastic member.

11 Claims, 7 Drawing Sheets

ABSORBENT ARTICLE

BACKGROUND OF THE INVENTION

1. Field of the Invention

The present invention relates to an absorbent article for absorbing and retaining a liquid waste such as menstrual blood and, more particularly, to an absorbent article enabled to absorb the liquid waste effectively in accordance with the motions of a wearer.

2. Related Art

In the prior art, there have been developed a variety of absorbent articles. In Unexamined Published Japanese Utility Model Application No. 7-33315, for example, there is disclosed an absorbent article (or a sanitary napkin) which aims at preventing the leakage of a menstrual blood when the wearer freely moves around.

The absorbent article disclosed in the Utility Model Application includes an upper napkin and a lower napkin, in each of which an absorbent core is covered with a liquid-permeable sheet. The upper napkin has a smaller inter-end edge size than that of the lower napkin and is positioned at the central portion of the lower napkin. From the two end edge portions of the upper napkin, moreover, there are extended a pair of elastic members extending in the longitudinal direction. These elastic members are fixed at their leading ends on the end edge portions of the lower napkin. These upper napkin and lower napkin can move relatively freely in accordance with the motions of the wearer without restraining each other.

However, the disclosed absorbent article has found it difficult to bring the upper napkin into close contact with the private part of the wearer because the upper napkin has a planar structure. What has been found especially difficult is to keep the contact with the private part while following the motions of the wearer. As a result, a clearance is formed between the upper napkin and the private part so that the discharged liquid is not absorbed by the upper napkin but is allowed to flow along the skin, thereby to cause a problem that the underwear is blotted with the discharged liquid. Therefore, the absorbent article has been liable to make the wearer feel uncomfortable.

SUMMARY OF THE INVENTION

The invention has an object to provide an absorbent article which is excellent in the followability to the motions of a wearer while keeping a close contact with the private part.

According to a first aspect of the invention, there is provided an absorbent article comprising: a liquid absorbing member including an absorbent core and a liquid-permeable sheet covering the liquid-receiving side of the absorbent core; a support body positioned on the lower side of the liquid absorbing member; and at least three elastic members for supporting the liquid absorbing member, each extending in the longitudinal direction of the absorbent article and being fixed at its front and rear end portions on the support body, one of the three elastic members being positioned at the widthwise central portion of the absorbent article, and wherein the front and rear fixed portions between the central elastic member and the support body are positioned longitudinally outwardly of those between the remaining elastic members and the support body, whereby the support body is bent in the longitudinal direction by the tensions of the elastic members, and the liquid absorbing member is deformed to bulge at its widthwise central portion away from the support body by the central elastic member.

For example, the absorbent core may be supported by the central elastic member and the remaining elastic members. Alternatively, the absorbent core may be supported by the central elastic member whereas the liquid-permeable sheet may be supported by the remaining elastic members.

In the first aspect of the invention thus far described, the liquid absorbing member having the absorbent core is supported in the floating state by the central elastic member and the remaining elastic members so that it can move freely of the support body. Moreover, the liquid absorbing member having the absorbent core is deformed to bulge at its widthwise central portion so that it can fit on the concave shape of the private part to reduce the leakage of the menstrual blood.

It should be noted that the central elastic member may be one, two or more, and the remaining elastic members may be two, four or more.

According to a second aspect of the invention, there is provided an absorbent article comprising: a support body; an absorbent core positioned on the liquid-receiving side of the support body; an elastic member for supporting the widthwise central portion of the absorbent core, the elastic member extending in the longitudinal direction of the absorbent article and being fixed at its front and rear end portions on the support body; and a liquid-permeable sheet covering the absorbent core and extended outwardly of the absorbent core in the widthwise direction, the extended portions of which are attached to the support body directly or through an auxiliary sheet rising from the support body, whereby the support body is bent in the longitudinal direction by the tension of the elastic member, and the absorbent core is deformed to bulge at its widthwise central portion away from the support body by the elastic member.

According to the second aspect of the invention, the absorbent core is supported at its two side portions by the extended portions of the liquid-permeable sheet and/or the auxiliary sheet rising from the support body and is deformed to bulge at its central portion by the elastic member. Therefore, the absorbent core has a degree of freedom with respect to the support body and easily fits on the private part.

In the above, elastic members extending in the longitudinal direction of the absorbent article may be attached to the extended portions of the liquid-permeable sheet and/or the auxiliary sheet, and fixed at their front and rear end portions to the support body. In this case, it is preferred that the front and rear fixed portions between the elastic member supporting the widthwise central portion of the absorbent core and the support body are positioned longitudinally outwardly of those between the elastic members attached to the extended portions of the liquid-permeable sheet and/or the auxiliary sheet and the support body.

Thus, the absorbent core may be deformed to bulge by the tensions of the elastic members disposed in the liquid-permeable sheet and/or the auxiliary sheet and by the tension of the elastic member disposed on the central portion of the absorbent core.

Alternatively, the extended portions of the liquid-permeable sheet and/or the auxiliary sheet may be given an elastically shrinking force in the widthwise direction of the absorbent article.

In the invention, moreover, the elastic member supporting the widthwise central portion of the absorbent core (or the central elastic member) preferably has a higher shrinking tension than that of the remaining elastic members.

Still moreover, the support body may include a second absorbent core positioned on the lower side of the aforementioned absorbent core. However, the support body may not have the absorbent core or may be provided with a thin absorbent sheet.

DESCRIPTION OF THE PREFERRED EMBODIMENTS

The invention will be described with reference to the accompanying drawings.

Figure 1:
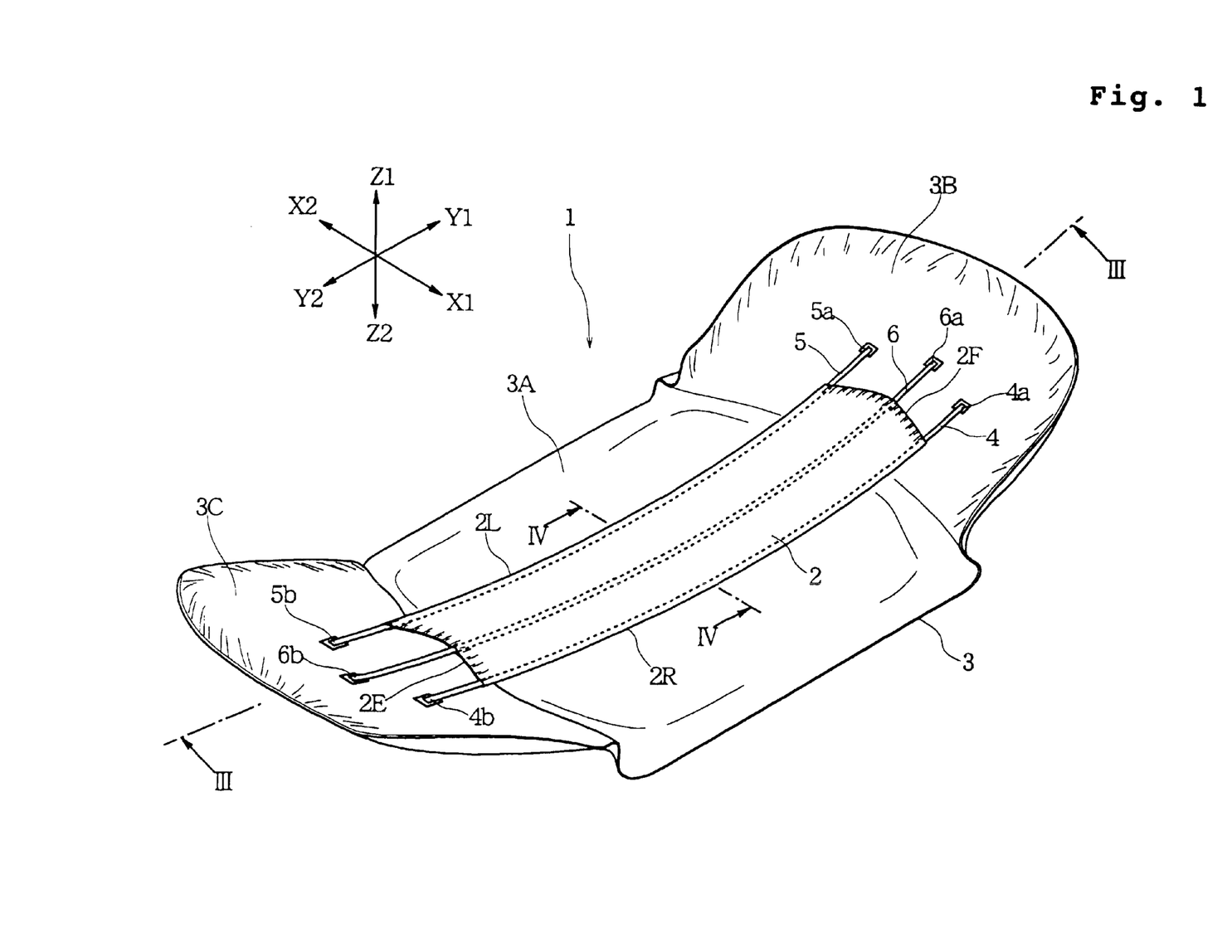
FIG. 1 is a perspective view showing a sanitary napkin as an absorbent article according to a first embodiment of the invention.
Figure 2:
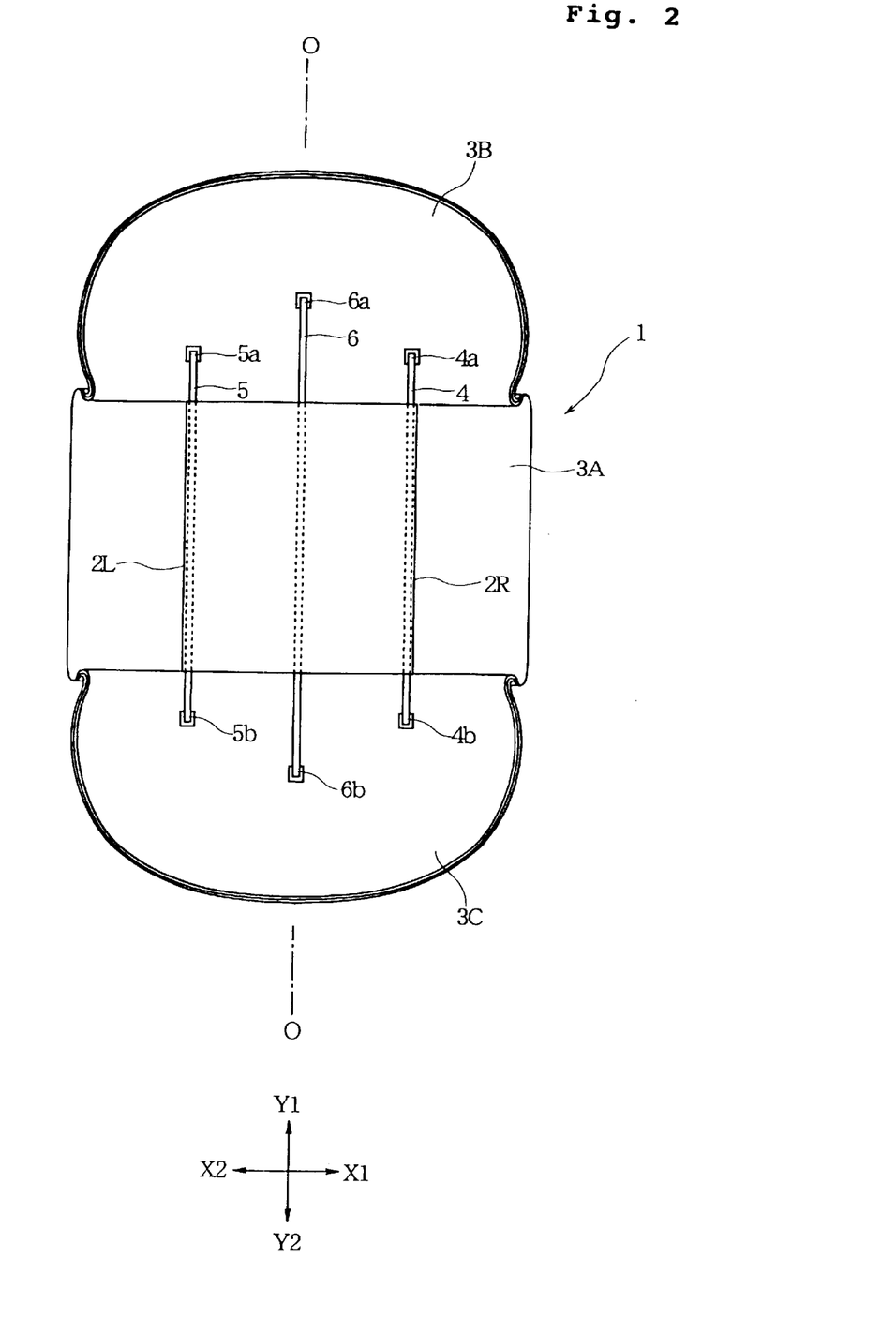
FIG. 2 is a top plan view of the sanitary napkin shown in FIG. 1.
Figure 3:
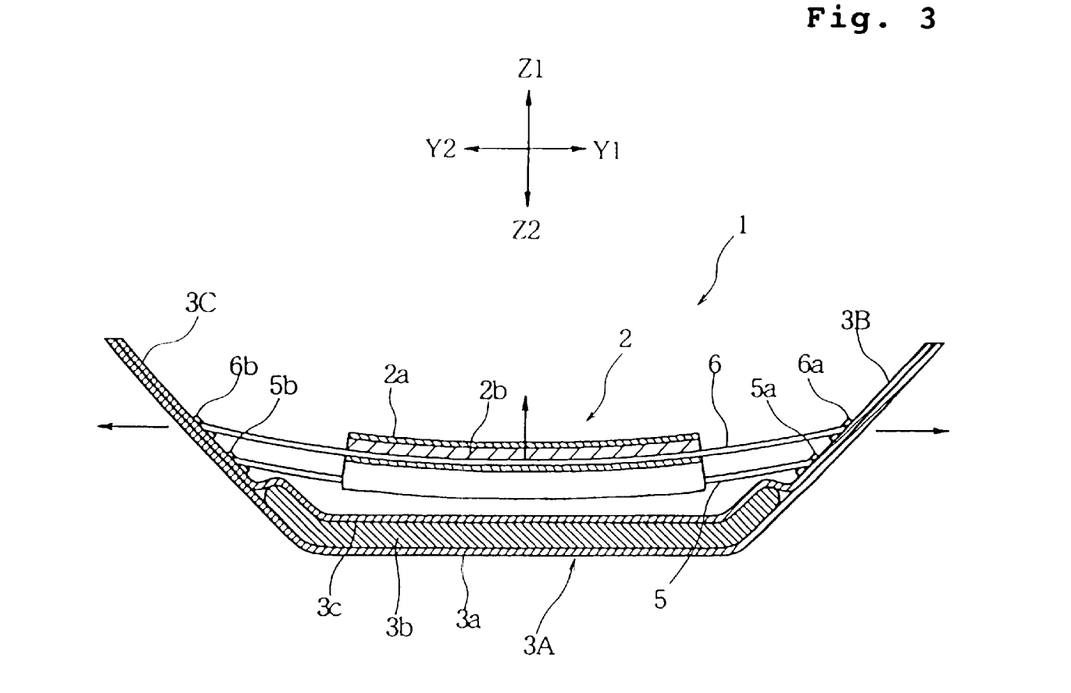
FIG. 3 is a sectional view taken along line III—III of FIG. 1.

FIG. 1 is a perspective view showing a sanitary napkin 1 as an absorbent article according to a first embodiment of the invention; FIG. 2 is a top plan view of the sanitary napkin 1 shown in FIG. 1; FIG. 3 is a sectional view taken along line III—III of FIG. 1; and FIGS. 4A and 4B are sectional views taken along line IV—IV of FIG. 1 when an absorbent core is flat and when the absorbent core is deformed, respectively.

In the sanitary napkin 1 shown in FIG. 1, the upper side (or the Z1 side) is the private part-facing side (or the liquid-receiving side), and the lower side (or the Z2 side) is the underwear-facing side. This sanitary napkin 1 is constructed to include a support body 3 disposed on the lower side and a liquid absorbing member 2 disposed on the upper side and at a spacing from the support body 3. In the drawings, the widthwise direction of the sanitary napkin 1 is indicated at X1–X2, and the longitudinal direction of the sanitary napkin 1 is indicated at Y1–Y2. In the liquid absorbing member 2, the side edge portions lying opposite one another in the widthwise direction (or in the transverse direction) are indicated at 2R and 2L, and the end edge portions lying opposite one another in the longitudinal direction are indicated at 2F and 2E.

Figure 4A:
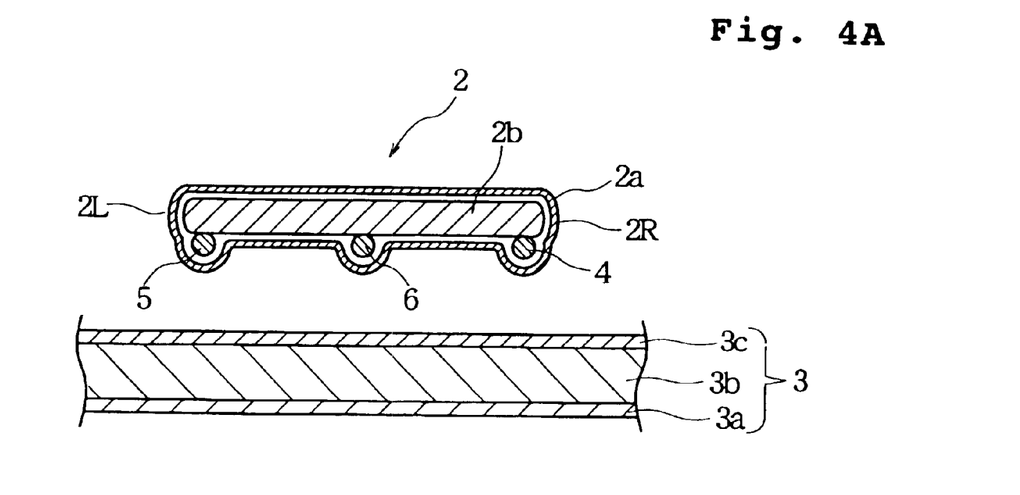
FIGS. 4A and 4B are sectional views taken along line IV—IV of FIG. 1 and show states before and after an absorbent core is deformed, respectively.
Figure 4B:
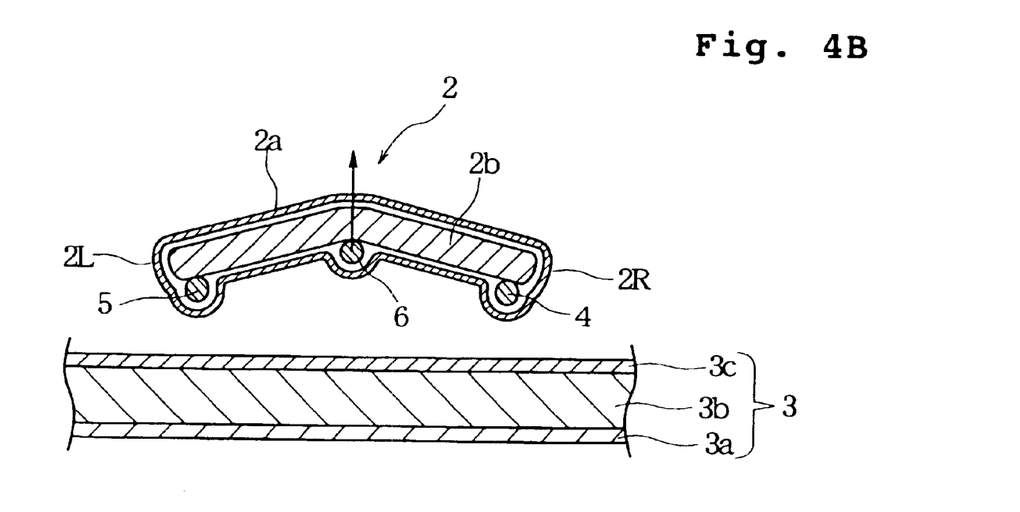

As shown in FIGS. 3, 4A and 4B, the liquid absorbing member 2 is constructed to include an absorbent core 2b having an excellent liquid absorbing and retaining capacity and a liquid-permeable sheet 2a enveloping the absorbent core 2b. This absorbent core 2b is formed by enveloping a mixture of pulp and a super absorbent polymer (SAP) by a liquid-permeable sheet such as tissue paper, for example.

The liquid-permeable sheet 2a is a nonwoven fabric made of PE fibers, PP fibers, PET fibers, as made hydrophilic (i.e., subjected to a hydrophilic treatment), or their composite fibers, such as a spun-bonded nonwoven fabric and a spun-laced nonwoven fabric.

The liquid-permeable sheet 2a and the absorbent core 2b are adhered with an olefin-based or rubber-based hot melt adhesive. The application of this hot melt adhesive is performed in a comb-, spray- or spiral-pattern to prevent the liquid permeability from dropping between the liquid-permeable sheet 2a and the absorbent core 2b.

The support body 3 is provided with a liquid-impermeable support sheet 3a. This support sheet 3a is formed of an air-permeable resin film or a spun-bonded or spun-laced nonwoven fabric made water-repellent or is prepared by joining the air-permeable resin film to the back of the nonwoven fabric. The support body 3 in this embodiment is further provided with a second absorbent core 3b on the support sheet 3a and a liquid-permeable sheet 3c covering the second absorbent core 3b. The second absorbent core 3b is prepared by enveloping pulp or a mixture of pulp and SAP by tissue paper or the like, or by overlapping sheets of absorbent paper, and the sheet 3c is a spun-bonded or spun-laced nonwoven fabric of fibers made hydrophilic.

The area of the liquid absorbing member 2 is made smaller than that of the support body 3, and especially the width size (or the size in the direction X1–X2) of the liquid absorbing member 2 is made smaller than the width size of a central portion 3A of the support body 3.

To the two widthwise side edge portions 2R and 2L of the liquid absorbing member 2, respectively, there are attached elastic members 4 and 5 which extend in the longitudinal direction. To the widthwise central portion (or the central portion in the direction X1–X2) of the liquid absorbing member 2, there is attached an elastic member 6 which is positioned midway between and generally in parallel with those elastic members 4 and 5. As shown in FIG. 2, the elastic member 6 is generally aligned with a longitudinally extending center line 0—0 of the sanitary napkin 1.

It should be noted that the term "the widthwise central portion of the absorbent core/liquid absorbing member" as used herein means a portion located midway between two side portions of the absorbent core/liquid absorbing member in the widthwise direction.

The elastic members 4, 5 and 6 can be made of any suitable material such as natural rubber, synthetic rubber, polyurethane or a styrene-butadiene copolymer and can be formed into a thread, filament, film or band shape. Alternatively, they may be prepared by cutting an stretchable nonwoven fabric.

In the structure shown in FIGS. 4A and 4B, the elastic members 4, 5 and 6 are disposed on the lower side of the absorbent core 2b of the liquid absorbing member 2 so that the absorbent core 2b is supported by those three elastic members 4, 5 and 6. These individual elastic members 4, 5 and 6 are extended in the longitudinal direction (i.e., in the direction Y1–Y2) from the individual end edge portions 2F and 2E of the liquid absorbing member 2. As shown in FIGS. 1 and 2, the front and rear end portions of the elastic members 4, 5 and 6 are fixed individually on a front portion 3B and a rear portion 3C of the support body 3. More specifically, the elastic members 4, 5 and 6 are fixed at the front fixed portions 4a, 5a and 6a on the front portion 3B of the support body 3, while at the rear fixed portions 4b, 5b and 6b on the rear portion 3C of the support body 3. Among the front fixed portions 4a, 5a and 6a on the Y1 side, the front fixed portions 6a is located outside of the remaining front fixed portions 4a and 5a in the longitudinal direction. Among the rear fixed portions 4b, 5b and 6b on the Y2 side, the rear fixed portions 6b is located outside of the remaining rear fixed portions 4b and 5b in the longitudinal direction. Therefore, when the sanitary napkin 1 is flattened, the length (or the size in the longitudinal direction) of the elastic member 6 is larger than that of the remaining elastic members 4 and 5.

In the packaged state of the sanitary napkin 1 before use, the front portion 3B and the rear portion 3C of the support body 3 are folded and laid over the central portion 3A to have a three-layered structure. At this time, the individual elastic members 4, 5 and 6 are in the shrunk states so that the absorbent core 2b of the liquid absorbing member 2 is generally in a flat state, as shown in FIG. 4A, and is laid over the support body 3.

When this sanitary napkin 1 is to be used, the front portion 3B and the rear portion 3C of the support body 3 are expanded in the longitudinal direction (i.e., in the direction Y1–Y2). At this time, by the elastic forces (or the tensile forces) of the individual elastic members 4, 5 and 6, the front portion 3B and the rear portion 3C are bent to rise from the central portion 3A, or the support body 3 is curved in the longitudinal direction, as shown in FIGS. 1 to 3.

As described hereinbefore, the front and rear fixed portions 6a and 6b between the central elastic member 6 and the support body 3 are positioned longitudinally outwardly of the front and rear fixed portions 4a and 4b, and 5a and 5b between the remaining elastic members 4 and 5 and the support body 3. When the support body 3 is bent and deformed in the longitudinal direction, as shown in FIGS. 1 and 3, therefore, the central elastic member 6 is spaced apart in the height direction (or the direction Z1–Z2) from the support body 3 by a larger distance than the elastic members 4 and 5 on the two sides.

As shown in FIG. 4B, therefore, the lower face of the center of the absorbent core 2b is raised toward the Z1 side by the elastic member 6. As a result, the liquid absorbing member 2 is so folded or curved that the two side edge portions 2R and 2L are directed downward (or toward the Z2 side) while the widthwise central portion between the two side edge portions 2R and 2L bulges to the wearer.

When the liquid absorbing member 2 is supported at a floating position over the support body 3 by the elastic members 4, 5 and 6, and when the central portion of the liquid absorbing member 2 is so bulged as can readily fit on the private part of the wearer, the liquid absorbing member 2 having the absorbent core 2b can move freely over the support body 3 in accordance with the motions of the wearer's body while fitting on the private part. Therefore, the liquid absorbing member 2 can reliably absorb the discharged liquid so that the sideway leakage of the liquid from the liquid absorbing member 2 can be effectively prevented, thereby to solve such a problem of the prior art as might otherwise blot the underwear. In addition, when the liquid absorbing member 2 is in contact with the private part of the wearer, the liquid absorbing member 2 is pushed down to contact lightly with the second absorbent core 3b of the support body 3 (through the sheet 3c), so that the menstrual blood having passed through the absorbent core 2b or having leaked to the two sides of the liquid absorbing member 2 can be absorbed by the second absorbent core 3b.

Thus, the liquid absorbing member 2 in the free state can always come into close contact with the private part of the wearer to absorb and retain the menstrual blood sufficiently by the absorbent core 2. Therefore, the second absorbent core 3b of the support body 3 may be made so thin as can be prepared by overlaying sheets of absorbent paper such as tissue paper, so that the napkin can be thinned in its entirety.

In the construction thus far described, the shrinking tension of the central elastic member 6 is preferred to be set higher than that of the two side elastic members 4 and 5. This results in the central elastic member 6 being reluctant to warp, when the sanitary napkin 1 is curved as shown in FIGS. 1 and 3, so that the force to raise the central portion of the absorbent core 2b is intensified by the elastic member 6. As a result, the absorbent core 2b can be easily deformed, as shown in FIG. 4B.

The tension of the central elastic member 6 can be set higher, either by making the longitudinal elastic coefficient of the elastic member 6 larger than that of the elastic members 4 and 5, or by fixing the individual elastic members 4, 5 and 6 on the support body 3 being flat while the elastic member 6 being extended longer than the elastic members 4 and 5.

Figure 5A:
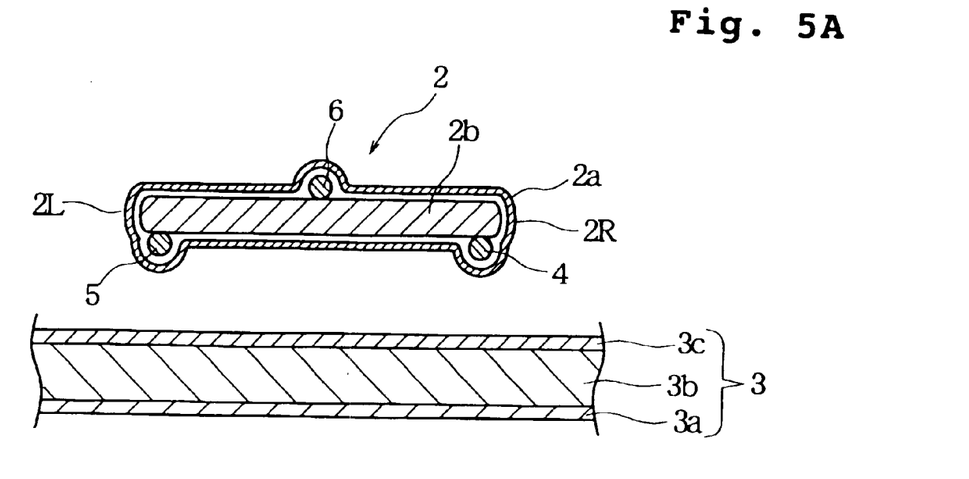
FIGS. 5A and 5B are sectional views similar to those of FIGS. 4A and 4B and show a modification of the embodiment of FIG. 1 in states before and after the absorbent core is deformed, respectively.
Figure 5B:
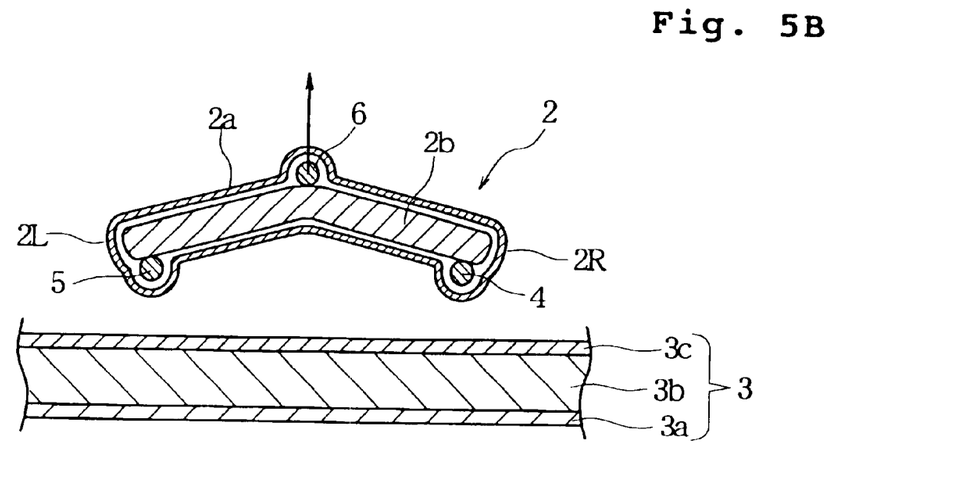

FIGS. 5A and 5B show a modification of the first embodiment. FIG. 5A shows the state in which the absorbent core 2b is flat, and FIG. 5B shows the state in which the absorbent core 2b is deformed.

The liquid absorbing member 2 shown in FIGS. 5A and 5B is different from the liquid absorbing member 2 shown in FIGS. 4A and 4B, only in that the central elastic member 6 is interposed between the liquid-permeable sheet 2a and the upper face of the absorbent core 2b. In this sanitary napkin, the absorbent core 2b is suspended upward by the central elastic member 6. As a result, the absorbent core 2b is deformed at its central portion to bulge to the wearer, as shown in FIG. 5B.

Figure 6:
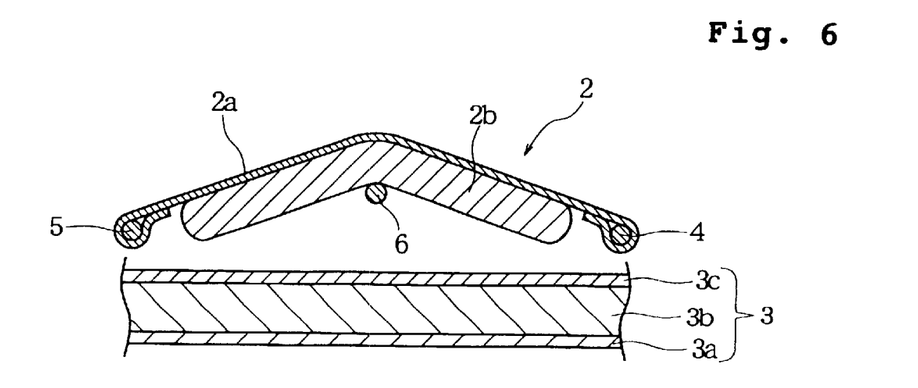
FIG. 6 is a sectional view similar to that of FIG. 4B but shows another modification of the embodiment of FIG. 1.

FIG. 6 is a sectional view showing another modification of the first embodiment at the same portion as in FIGS. 4A and 4B.

In the modification shown in FIG. 6, the absorbent core 2b forming the liquid absorbing member 2 is prepared by enveloping either pulp or a mixture of pulp and SAP by tissue paper, a liquid-permeable nonwoven fabric or the like, and the liquid-permeable sheet 2a is attached to the liquid-receiving side of the absorbent core 2b. The central elastic member 6 is attached to the widthwise central portion of the absorbent core 2b, but the two side elastic members 4 and 5 are attached to the two side portions of the liquid-permeable sheet 2a which extend outwardly of the absorbent core 2b.

In this modification, too, the front and rear fixed portions 6a and 6b between the central elastic member 6 and the support body 3 are positioned longitudinally outwardly of the front and rear fixed portions 4a and 4b, and 5a and 5b between the individual elastic members 4 and 5 and the support body 3, as shown in FIG. 2. Therefore, the widthwise central portion of the absorbent core 2b is deformed to bulge to the wearer by the central elastic member 6.

It should be noted that, throughout the embodiments of FIGS. 1 to 6, two or more elastic members 6 may be provided, and/or two or more elastic members 4 and 5 may be individually provided. For example, in the construction shown in FIG. 6, there may be provided two elastic members 4 and two elastic members 5. In this case, at each side of the liquid absorbing member 2, one of the two elastic members may be attached to the absorbent core 2b; the other of the two elastic members may be attached to the liquid-permeable sheet 2a.

Figure 7:
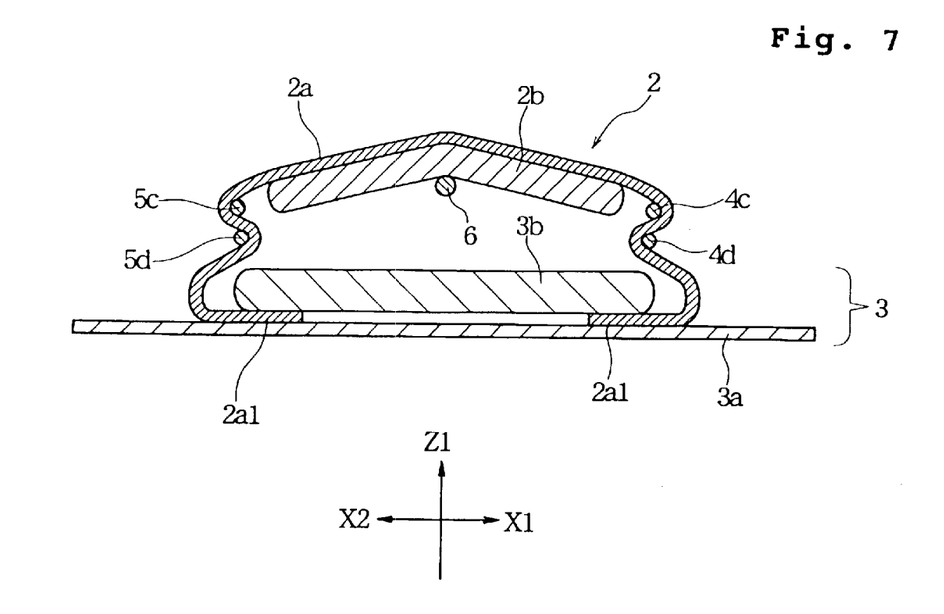
FIG. 7 is a sectional view similar to that of FIG. 4B but shows a sanitary napkin as an absorbent article according to a second embodiment of the invention.

FIG. 7 is a sectional view similar to that of FIG. 4B but shows a sanitary napkin as an absorbent article according to a second embodiment of the invention.

In the sanitary napkin shown in FIG. 7, the support body 3 having the shape shown in FIGS. 1 to 3 is mainly constructed to include the liquid-impermeable support sheet 3a, and the second thin absorbent core 3b placed over the-support sheet 3a.

The liquid absorbing member 2 is constructed, as in the foregoing embodiment shown in FIG. 6, to include the absorbent core 2b prepared by enveloping pulp or a mixture of pulp and SAP by the liquid-permeable sheet, and the liquid-permeable sheet 2a attached to the liquid-receiving side surface of the absorbent core 2b.

In this second embodiment, however, the liquid-permeable sheet 2a is extended farther outwardly of the two side portions of the absorbent core 2b in the widthwise direction (or in the direction X1–X2), and its two side portions 2a1 and 2a1 are so attached to the support sheet 3a as to envelop the two side portions of the second absorbent core 3b.

The elastic member 6 is attached to the widthwise central portion of the absorbent core 2b, and elastic members 4c and 4d and elastic members 5c and 5d are attached to the two sideway extensions of the liquid-permeable sheet 2a. The individual elastic members 6, 4c and 4d, and 5c and 5d are extended generally in parallel with the longitudinal direction (or the direction Y1–Y2). As in the construction shown in FIG. 2, moreover, the front and rear fixed portions between the central elastic member 6 and the support sheet 3a of the support body 3 are positioned longitudinally outwardly of those between the remaining elastic members 4c and 4d, and 5c and 5d and the support sheet 3a of the support body 3.

When the sanitary napkin is to be used by expanding the support sheet 3a, this support sheet 3a is curved in the longitudinal direction by the shrinking tensions of the individual elastic members such that the central elastic member 6 is tensed at a higher position away from the support sheet 3a than the remaining elastic members 4c and 4d, and 5c and 5d. As a result, the absorbent core 2b is deformed at its widthwise central portion to bulge to the wearer. As shown in FIG. 7, moreover, the two sideway extensions of the liquid-permeable sheet 2a are corrugated by the elastic members 4c and 4d, and 5c and 5d provided thereon.

In this sanitary napkin, the bulging central portion of the absorbent core 2b can come into close contact with the private part of the wearer, and the absorbent core 2b per se can move freely independently of the support sheet 3a while fitting on the-private part. When the menstrual blood having passed through the absorbent core 2b is absorbed by the underlying second absorbent core 3b, the two sideway extensions of the liquid-permeable sheet 2a function to prevent the menstrual blood from further leaking to the widthwise outer sides. In addition, the menstrual blood, as might otherwise flow to the two sides of the sanitary napkin in the widthwise direction through the liquid-permeable sheet 2a, is guided along the liquid-permeable sheet 2a to the underlying second absorbent core 3b. This makes it possible to prevent the sideway leakage of the menstrual blood.

Moreover, since the two sideway extensions of the liquid-permeable sheet 2a are corrugated by the elastic members 4c and 4d, and 5c and 5d, the liquid-permeable sheet 2a can be folded on the support sheet 3a and the second absorbent core 3b without being extended toward the X1 and X2 sides, when the absorbent core 2b abuts against the private part of the wearer (through the liquid-permeable sheet 2a) so that the support body 3 is pushed onto the absorbent core 2b by the underwear. As a result, the liquid-permeable sheet 2a is not largely expanded sideways so that the menstrual blood having wetted the liquid-permeable sheet 2a can be prevented from leaking sideways from the support sheet 3a.

Figure 8:
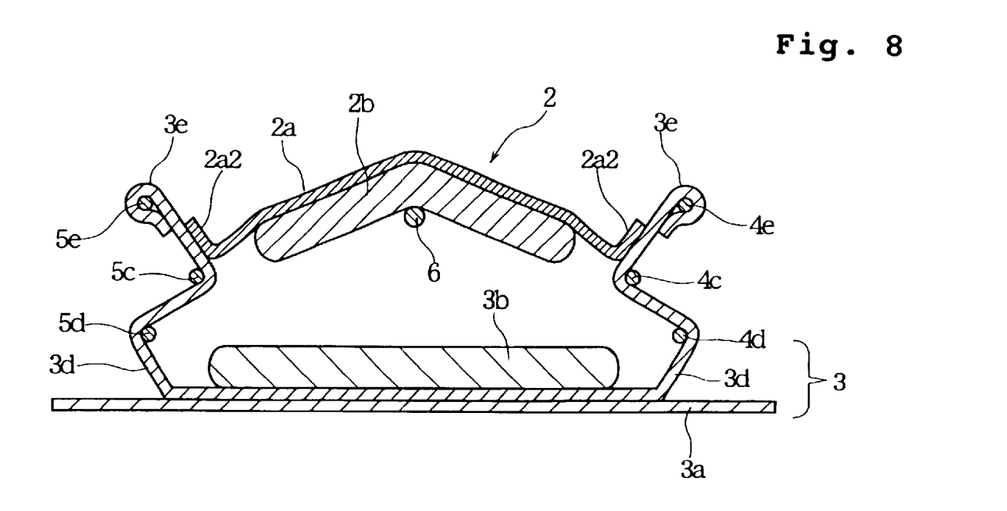
FIG. 8 is a sectional view showing a modification of the embodiment shown in FIG. 7.

FIG. 8 is a sectional view similar to that of FIG. 4B but shows a modification of the second embodiment shown in FIG. 7.

In the modification of FIG. 8, the support body 3 is provided with the liquid-impermeable support sheet 3a and the second absorbent core 3b. To the support sheet 3a, moreover, there is attached an auxiliary sheet 3d, two side portions of which rise from the positions outside of the second absorbent core 3b in the widthwise direction. In the liquid absorbing member 2, the liquid-permeable sheet 2a, as attached to the liquid-receiving side of the absorbent core 2b, is further attached at their two side portions 2a2 and 2a2 to the two side portions of the auxiliary sheet 3d.

This auxiliary sheet 3d may be formed of a spun-bonded nonwoven fabric being liquid-impermeable or made water-repellent. The two side portions of the auxiliary sheet 3d are further extended upward from their portions attached to the liquid-permeable sheet 2a to form leakage preventing cuffs (or leakage preventing walls) 3e and 3e rising from the two side portions of the absorbent core 2b.

The elastic member 6 is attached to the central portion of the absorbent core 2b, and the elastic members 4c and 4d, and 5c and 5d are attached to the two side portions of the auxiliary sheet 3d. As described hereinbefore, the front and rear fixed portions between the central elastic member 6 and the support sheet 3a of the support body 3 are positioned longitudinally outwardly of the front and rear fixed portions between the remaining elastic members 4c and 4d, and 5c and 5d and the support sheet 3a.

Like the construction shown in FIG. 7, therefore, the absorbent core 2b is deformed to bulge at its central portion, and the two side portions of the auxiliary sheet 3d are corrugated. To the upper ends of the leakage preventing cuffs 3e and 3e, there are attached cuff elastic members 4e and 5e for exhibiting the shrinking tensions. These cuff elastic members 4e and 5e are attached at their two longitudinal end portions to the support sheet 3a so that the leakage preventing cuffs 3e and 3e rise from the two sides of the absorbent core 2b as the support sheet 3a is curved in the longitudinal direction.

In this modification, between the two side portions of the absorbent core 2b and those of the second absorbent core 3b, there are provided the two side portions of the auxiliary sheet 3d which is formed of a liquid-impermeable or water-repellent sheet. Therefore, the menstrual blood having passed through the absorbent core 2b can be prevented from leaking sideways before it is absorbed by the second absorbent core 3b. Moreover, the two side portions of the auxiliary sheet 3d rise from the two side portions of the absorbent core 2b to form the leakage preventing cuffs 3e and 3e so that the sideway leakage can be prevented by the leakage preventing cuffs 3e and 3e.

It should be noted that, the single auxiliary sheet 3d is used to form the leakage preventing cuffs 3e and 3e in the embodiment of FIG. 8, but two separate auxiliary sheets 3d and 3d may be provided to individually form the leakage preventing cuffs 3e and 3e.

In the embodiments of FIGS. 7 and 8, the same elastic members 4 and 5 as those shown in FIGS. 4A and 4B may be optionally disposed on the two side portions of the absorbent core 2b.

It should be noted that the embodiments shown in FIGS. 7 and 8 can take a structure, from which the elastic members 4c and 4d, and 5c and 5d are omitted. In this case, the two widthwise side portions of the absorbent core 2b can be directed downward by shortening the size of the sheet portions extending and connecting between the two widthwise side portions of the absorbent core 2b and the support sheet 3a. Specifically, if the size of the sideway extensions of the liquid-permeable sheet 2a shown in FIG. 7 is shortened in the height direction or if the rising size of the two side portions of the auxiliary sheet 3d shown in FIG. 8 is shortened in the height direction, the liquid-permeable sheet 2a or the auxiliary sheet 3d can exhibit a restricting force to retain the two widthwise side portions of the absorbent core 2b at positions close to the support sheet 3a. By intensifying the shrinking tension of the central elastic member 6, therefore, the absorbent core 2b can be deformed to bulge, and this state can be kept even when the sanitary napkin is worn.

Figure 9:
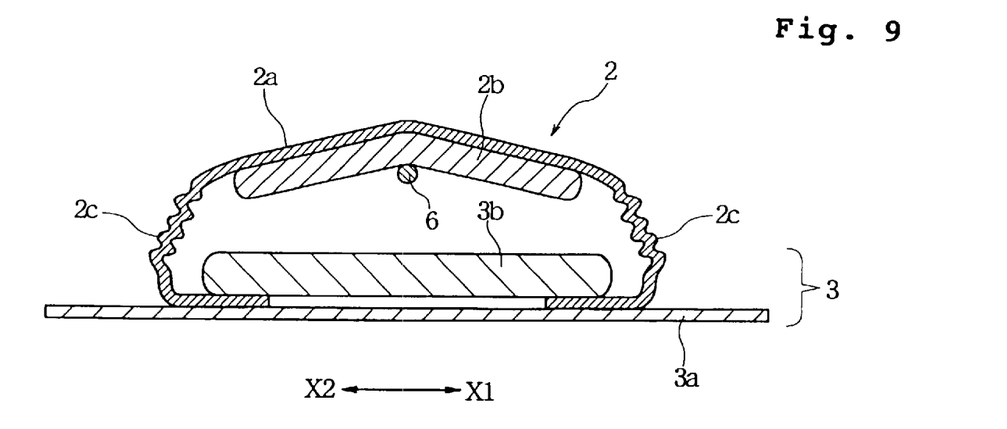
FIG. 9 is a sectional view showing another modification of the embodiment shown in FIG. 7.

FIG. 9 is a sectional view similar to that of FIG. 4B but shows a more preferable modification of the structure which is not provided with the elastic members 4c and 4d, and 5c and 5d.

In the modification shown in FIG. 9, the elastic members 4c and 4d, and 5c and 5d are removed from the embodiment shown in FIG. 7, but the liquid-permeable sheet 2a is given an elastic shrinking force in the widthwise direction (or in the direction X1–X2) at least in its sideway extensions (or the portions extending to the two sides from the absorbent core 2b). This absorbent core 2b is attracted at its two side portions to the support sheet 3a by elastically shrinking portions 2c and 2c, so that it can be deformed to bulge, while it abuts against the private part of the wearer, by that attracting force and the shrinking tension of the elastic member 6.

It should be noted that the liquid-permeable sheet 2a may exhibit the elastic shrinking force in its entirety in the widthwise direction. Alternatively, in the embodiment of FIG. 8, the two side portions of the auxiliary sheet 3d rising from the support sheet 3a may exhibit the elastic shrinking forces in the widthwise direction.

In order that the sheet may exhibit the elastic shrinking force, the liquid-permeable sheet 2a or the auxiliary sheet 3d can be formed of a nonwoven fabric containing crimped fibers. Alternatively, the liquid-permeable sheet 2a or the auxiliary sheet 3d may be prepared by adhering an elastic member such as rubber stretchable in the direction. X1–X2 to a nonwoven fabric in a stretched state.

According to the invention, as has been described in detail, the absorbent core can move independently of the support body and is deformed to bulge at its central portion so that its crest can bring into close contact with the private part of the wearer at all times. In this state, moreover, the absorbent core can follow the motions of the wearer so that it can absorb the discharging liquid reliably and effectively.

Although various exemplary embodiments have been shown and described, the invention is not limited to the embodiments shown. Therefore, the scope of the invention is intended to be limited solely by the scope of the claims that follow.

What is claimed is:

1. An absorbent article comprising:
   a liquid absorbing member including an absorbent core and a liquid-permeable sheet covering a liquid-receiving side of said absorbent core;
   a support body positioned on a lower side of said liquid absorbing member; and
   at least three elastic members for supporting said liquid absorbing member, each extending in a longitudinal direction of said absorbent article and being fixed at its front and rear end portions on said support body, one of said three elastic members being positioned at a widthwise central portion of said absorbent article, and
   wherein the front and rear fixed portions between said central elastic member and said support body are positioned longitudinally outwardly of those between remaining elastic members and said support body,
   whereby said support body is bent in the longitudinal direction by tensions of said elastic members, and said liquid absorbing member is deformed to bulge at its widthwise central portion away from said support body by said central elastic member.

2. The absorbent article as set forth in claim 1, wherein said absorbent core is supported by said central elastic member and said remaining elastic members.

3. The absorbent article as set forth in claim 1, wherein said absorbent core is supported by said central elastic member whereas said liquid-permeable sheet is supported by said remaining elastic members.

4. The absorbent article as set forth in claim 1, wherein said central elastic member has a higher shrinking tension than that of said remaining elastic members.

5. The absorbent article as set forth in claim 1, wherein said support body includes a second absorbent core positioned on the lower side of said absorbent core of said liquid absorbing member.

6. An absorbent article comprising:
   a support body; an absorbent core positioned on the liquid-receiving side of said support body;
   an elastic member for supporting a widthwise central portion of said absorbent core, the elastic member extending in a longitudinal direction of said absorbent article having front and rear end portions which are fixed on said support body; and
   a liquid-permeable sheet covering said absorbent core and extended outwardly of said absorbent core in a widthwise direction, extended portions of which are attached to said support body directly or through an auxiliary sheet rising from said support body,
   whereby said support body is bent in the longitudinal direction by a tension of said elastic member, and said absorbent core is deformed to bulge at its widthwise central portion away from said support body by said elastic member.

7. The absorbent article as set forth in claim 6, wherein elastic members extending in the longitudinal direction of said absorbent article are attached to the extended portions of said liquid-permeable sheet and/or said auxiliary sheet, and fixed at their front and rear end portions to said support body.

8. The absorbent article as set forth in claim 6, wherein the extended portions of said liquid-permeable sheet and/or said-auxiliary sheet are given an elastically shrinking force in the widthwise direction of said absorbent article.

9. The absorbent article as set forth in claim 6, wherein said support body includes a second absorbent core positioned below said absorbent core supported by said elastic member.

10. The absorbent article as set forth in claim 7, wherein the front and rear fixed portions between said elastic member supporting the widthwise central portion of said absorbent core and said support body are positioned longitudinally outwardly of those between said elastic members attached to the extended portions of said liquid-permeable sheet and/or said auxiliary sheet and said support body.

11. The absorbent article as set forth in claim 7, wherein said elastic member supporting the widthwise central portion of said absorbent core has a higher shrinking tension than that of said elastic members attached to the extended portions of said liquid-permeable sheet and/or said auxiliary sheet.

* * * * *